United States Patent [19]

Moroe et al.

[11] 4,214,110

[45] Jul. 22, 1980

[54] PROCESS FOR PRODUCING HYDROCARBONS

[75] Inventors: Tatsuo Moroe, Musashino; Akira Komatsu, Tokyo; Kiyosumi Doi, Fujisawa; Mitio Moroe, Musashino, all of Japan

[73] Assignee: Takasago Perfumery Co., Ltd., Tokyo, Japan

[21] Appl. No.: 708,246

[22] Filed: Jul. 23, 1976

Related U.S. Application Data

[63] Continuation of Ser. No. 523,782, Nov. 13, 1974, abandoned.

[30] Foreign Application Priority Data

Nov. 15, 1973 [JP] Japan .................................. 48-128650

[51] Int. Cl.² .................................................. C07C 3/26
[52] U.S. Cl. .................................... 585/241; 585/256; 585/752
[58] Field of Search ........ 260/677 R, 676 R, 683 PD; 585/241

[56] References Cited

U.S. PATENT DOCUMENTS 3,772,242  11/1973  Liska et al. .......................... 260/683

OTHER PUBLICATIONS

Kirk–Othmer, *Encyclopedia of Chemical Technology*, vol. 7, "Elastomers, Synthetic," p. 677, 1966.
Madorsky; "Pyrolysis of Hydrocarbon Polymers," *Science*, vol. III, pp. 360–361, 1950.

*Primary Examiner*—C. Davis
*Attorney, Agent, or Firm*—Sughrue, Rothwell, Mion, Zinn and Macpeak

[57] ABSTRACT

A process for producing hydrocarbons having about 10 to 50 carbon atoms with a high yield by subjecting a synthetic polyisoprene rubber to a thermally destructive distillation under a reduced pressure and further a process for producing squalane-like saturated hydrocarbons by catalytically reducing the distillate thus obtained from the synthetic polyisoprene rubber.

2 Claims, No Drawings

PROCESS FOR PRODUCING HYDROCARBONS

BACKGROUND OF THE INVENTION

1. Field of the Invention

The present invention relates to a process for producing hydrocarbons and more particularly it relates to a process of producing hydrocarbons having about 10 to 50 carbon atoms by thermally decomposing a synthetic polyisoprene rubber. The invention further relates to a process for producing saturated hydrocarbons, in particular squalane-like saturated hydrocarbons having 25 to 35 carbon atoms, comprising catalytically reducing the hydrocarbons thus obtained from the synthetic polyisoprene rubber.

2. Description of the Prior Art

A synthetic polyisoprene rubber is a synthetic rubber similar to a natural rubber and having 92 to 97% cis-type double bonds obtained by polymerizing isoprene in the presence of a Ziegler type catalyst or a lithium-type catalyst and recently such a rubber has become commercially available easily and at a low cost.

However, it is quite difficult economically to obtain low-polymer hydrocarbons by the oligomerization of isoprene. Therefore, various investigations have been made on the thermal decomposition of easily available synthetic polyisoprene rubber for the purpose of producing low-polymer hydrocarbons and as the results it has been discovered that different from natural rubbers, synthetic polyisoprene rubber provides low-polymer hydrocarbons, in particular hydrocarbons having about 10 to 50 carbon atoms with quite a high yield by the thermal decomposition of synthetic polyisoprene rubber.

Furthermore, by continuing the investigations, it has also been discovered that squalane-like saturated hydrocarbons having about 25 to 35 carbon atoms can be also obtained by catalytically reducing the hydrocarbons obtained from the synthetic polyisoprene rubber.

SUMMARY OF THE INVENTION

Therefore, according to the present invention there is provided a process for producing hydrocarbons which comprises subjecting a synthetic polyisoprene rubber to a thermally destructive distillation under a reduced pressure.

Furthermore, according to the present invention there is further provided a process of producing saturated hydrocarbons which comprises subjecting a synthetic polyisoprene rubber to a thermally destructive distillation under a reduced pressure and then catalytically reducing the distillate thus obtained.

DETAILED DESCRIPTION OF THE INVENTION

It is well known that low-polymer hydrocarbons are obtained by thermally decomposing natural rubber and, in particular, as a method of thermally decomposing natural rubber under a reduced pressure, a method has been reported wherein subjecting natural rubber to a thermally destructive distillation under a reduced pressure of 0.1 mm. Hg, a distillate in an amount of 63.5% and resinous materials in an amount of 36.5% as disclosed in Staudinger & Fritschi; Helv. Chim. Acta. ;Vol. 5, 785(1922) are obtained.

On the other hand, however, it has been discovered that when synthetic polyisoprene rubber is used as the raw material in the thermal decomposition, the following remarkably excellent results are obtained as compared with the case of using natural rubber as the raw material.

(1). While about five hours are required to distill the decomposition products in the thermal decomposition of natural rubber under reduced pressure, the distillatin can be almost completely finished in only about 30 minutes in the thermal decomposition of the synthetic polyisoprene rubber.

(2). While a large amount of resinous materials are formed in the thermal decomposition of natural rubber, such resinous materials are scarcely formed in the thermal decomposition of the synthetic polyisoprene rubber.

(3). While the content of the hydrocarbons having about 25 to 35 carbon atoms in the product or distillate is less than about 20% in the case of using natural rubber, the content is higher than about 60% in the case of using the synthetic polyisoprene rubber.

(4). While the product obtained from natural rubber has a bad odor caused by the decomposition of impurities, the product obtained from the synthetic polyisoprene does not have such a bad odor and further by catalytically reducing the product, saturated hydrocarbons having properties superior to squalane can be obtained, these saturated hydrocarbons thus being useful as bases for cosmetics, cold resistant lubricating oils, etc.

The polyisoprene rubber as used in this invention has 92 to 97% cis-type double bonds, has a mean molecular weight of about 220,000 and has the following general formular for repeating units contained in the polyisoprene rubber;

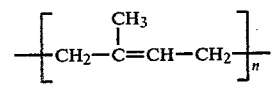

Typical commercial examples of the synthetic polyisoprene rubber are "IR2200" which is a common trademark of Japan Synthetic Rubber Co., Ltd., Kuraray Co., Ltd., Nippon zeon Co., Ltd., etc. the synthetic polyisoprene rubber can be prepared as described in F. W. Stravely, Industrial and Engineering Chemistry 48, No. 4, 778–783 (1956), etc., by polymerizing isoprene in the presence of a Ziegler type catalyst or a lithium-type catalyst.

As described above, by using synthetic polyisoprene rubber as the raw material in the process of this invention, excellent industrial advantages which have never been obtained and would not be expected in the case of using natural rubber can be obtained.

In the practice of the process of this invention, small pieces of synthetic polyisoprene rubber are uniformly heated under a reduced pressure of about 0.1 to 5 mm. Hg, preferably 0.1 to 1.0 mm. Hg. In this case it is preferable to conduct the evacuation, while introducing an inert gas such as nitrogen gas, carbon dioxide gas, etc., into the heating zone. The heating temperature is about 300 to 400° C., preferably 340 to 350° C. and better results are obtained when the raw material is uniformly heated using electric heating, heat transfer medium, etc. Thus, the synthetic polyisoprene rubber is melted, decomposed after a period of time, and then hydrocarbons having about 10 to 50 carbon atoms are distilled at a temperature of about 40 to 260° C. when the pressure is 1.0 mm. Hg. The thermaly destructive distillation can be suitably accomplished in about 30 minutes at about 350° C when 1 Kg of the starting material rubber is used. The distillate obtained can be further separated into each component by distilling under reduced pressure. A typical composition of the fractions thus obtained is shown in the following table.

Table 1

| No. | Boiling Point (1.0 mm. Hg) | Number of Carbon Atoms | Yield (%) |
|---|---|---|---|
| 1 | 40–60 | 10 | 20 |
| 2 | 80–130 | 15–20 | 8.6 |
| 3 | 155–240 | 25–35 | 65.4 |
| 4 | 240 and above | 40–50 | 5 |

Fraction No. 1 is dipentene having a purity of 98% and Fraction No. 2 comprises chain and cyclic unsaturated terpene compounds. Fractions No. 1 and No. 2 can be used as raw materials for perfumes. Fractions No. 3 and No. 4 comprise chain unsaturated terpene compounds.

Fraction No. 3 is the main fraction of components having about 25 to 35 carbon atoms which cmprise 65.4% of the total fraction components and when the fraction is subjected to a catalytic reduction at normal pressure or under pressure, e.g., about 50 to 200 $Kg/cm^2$, in the presence of a catalyst such as palladium, nickel, platinum, etc., using a conventional catalytic reduction method with hydrogen, saturated hydrocarbons are obtained. The catalytic reduction is generally conducted at about room temperature (e.g., 20 to 30° C) to about 300° C. When palladium and platinum are used as a catalyst, a suitable temperature generally ranges from about room temperature to about 100° C, and, when nickel is used as a catalyst, a suitable temperature generally ranges from about 100° to about 300° C, preferably about 250° C. When nickel is used as a catalyst, the reaction generally is completed in about 5 to 10 hours at about 250° C. The amount of hydrogen generally employed is a sufficient amount to satisfy hydrogen absorption completion and a suitable amount of the catalyst generally ranges from about 3 to 10% by weight based on the raw materials. The ratio of the hydrocarbons having about 25, 30, and 35 carbon atoms in the saturated hydrocarbons is about 13:65:22, that is, the saturated hydrocarbons are mainly composed of hydrocarbons having about 30 carbon atoms. The properties of the saturated hydrocarbons together with the properties of squalane are shown in the following table.

Table 2

| Property | Saturated Hydrocarbons (mainly $C_{30}$) | Saturated Hydrocarbons ($C_{25}$–$C_{35}$) | Squalene |
|---|---|---|---|
| Boiling Point (1.0 mm. Hg) | 195–215 | 155–240 | 205–215 |
| Specific Gravity ($d_{20}^{20}$) | 0.8988 | 0.8729 | 0.8106 |
| Freezing Point* | ab. −70° C. | ab. −70° C. | ab. −55° C. |
| Iodine Value | 0 | 0 | 0 |

*Simple measurement in an acetone-dry ice bath.

As is clear from the results shown in Table 2, the saturated hydrocarbons obtained by the process of this invention have a lower freezing point than squalane and also are superior in other properties to natural squalane. Thus the saturated hydrocarbons can be advantageously used as bases for cosmetics as disclosed in U.S. Patent Application Ser. No. 523,783, filed Nov. 13, 1974 and now abandoned (corresponding to Japanese Patent Application 127870/1973) and medicaments as well as raw materials for lubricating oils.

The invention will be explained in greater detail by referring to the following comparison example and the examples of this invention.

COMPARISON EXAMPLE

In a decomposition flask was charged 100 g. of natural raw rubber and after displacing the inside atmosphere of the flask with nitrogen and then evacuating the flask, the natural raw rubber was heated to 350–390° C. using an electric heater under a pressure of 0.1 mm. Hg, whereby the decomposition of the rubber began after 15 minutes and was finished after 5 hours. After the decomposition was completed, 40 g. of a resinous material remained in the flask and when the resinous material was heated to temperatures higher than 400° C., the material was not decomposed. By subjecting the distillate obtained to a fractional distillation, 31.6 g. of a fraction (dipentene) boiling at 40–50° C./0.1 mm. Hg and 28.4 g. of a fraction oiling at 120–260° C./0.1 mm. Hg were obtained.

EXAMPLE 1

In a decomposition flask were charged 100 g. of small pieces of a synthetic polyisoprene rubber and after displacing the inside atmosphere of the flask with nitrogen, the synthetic polyisoprene rubber was heated to 340–350° C. under a pressure of 0.1 mm. Hg, whereby the decomposition began after 17 minutes and 100 g. of distillate was obtained 13 minutes later with almost no residue being left in the flask.

The distillate obtained had the properties as shown in Table 1.

Example 2

In an autoclave, 100 g. of the distillate obtained in Example 1 was subjected to a hydrogenation in the presence of 10 g. of a Raney nickel catalyst at a temperature of 100° C. and a hydrogen pressure of 100 kg./cm.$^2$ The hydrogenation was finished after 2 hours. After cooling, the hydrogenated product was withdrawn from the autoclave and after removing the catalyst by filtration, distilled under a reduced pressure to provide 20 g. of a fraction (paramenthane) boiling at 40–60° C./0.1 mm. Hg and 80 g. of a high boiling fraction boiling at 120–260° C./0.1 mm. Hg. The high boiling fraction had the properties as shown in Table 2.

While the invention has been described in detail and with reference to specific embodiments thereof, it will be apparent to one skilled in the art that various changes and modifications can be made therein without departing from the spirit and scope thereof.

What is claimed is:

1. A process for producing a hydrocarbon product consisting essentially of hydrocarbons having about 10 to 50 carbon atoms with 60% or more of said product consisting of hydrocarbons containing 25 to 35 carbon atoms which comprises subjecting a synthetic polyisoprene rubber having 92 to 97% cis-type double bonds to a thermally destructive distillation at about 300 to 400° C for about 30 minutes under a reduced pressure of about 0.1 to 5 mm. Hg. to obtain said hydrocarbon product consisting essentially of hydrocarbons having about 10 to 50 carbon atoms with 60% or more of said product consisting of hydrocarbons containing 25 to 35 carbon atoms, said hydrocarbon product not having a bad odor and containing scarcely any resinous material.

2. A process for producing a hydrocarbon product consisting essentially of saturated hydrocarbons having about 10 to 50 carbon atoms with 60% or more of said product consisting of hydrocarbons containing 25 to 35 carbon atoms which comprises subjecting a synthetic polyisoprene rubber having 92 to 97% cis-type double bonds to a thermally destructive distillation at about 300° to 400° c. for about 30 minutes under a reduced pressure of about 0.1 to 5 mm. Hg to produce a hydrocarbon product consisting essentially of hydrocarbons having about 10 to 50 carbon atoms with 60% or more of said product consisting of hydrocarbons containing 25 to 35 carbon atoms, said hydrocarbon product containing scarcely any resinous material and not having a bad odor, and then catalytically reducing the distillate thus obtained with hydrogen to obtain said product consisting essentially of saturated hydrocarbons having about 10 to 50 carbon atoms with 60% or more of said saturated hydrocarbon product consisting of saturated hydrocarbons containing 25 to 35 carbon atoms.

* * * * *